(12) United States Patent
Johnson et al.

(10) Patent No.: US 7,052,467 B2
(45) Date of Patent: May 30, 2006

(54) STETHOSCOPIC SYSTEMS AND METHODS

(75) Inventors: Shawn C. D. Johnson, Winchester, MA (US); David S. Geller, 9 Tidd Cir., Lexington, MA (US) 02420

(73) Assignees: Shawn D. Johnson, Winchester, MA (US); David S. Geller, Lexington, MA (US)

(*) Notice: Subject to any disclaimer, the term of this patent is extended or adjusted under 35 U.S.C. 154(b) by 616 days.

(21) Appl. No.: 10/265,095

(22) Filed: Oct. 4, 2002

(65) Prior Publication Data

US 2004/0068194 A1    Apr. 8, 2004

(51) Int. Cl.
    *A61B 5/02*    (2006.01)
(52) U.S. Cl. .................. 600/528; 379/106.02
(58) Field of Classification Search ............ 600/528, 600/586; 379/106.02, 106.01; 381/67; 181/126, 181/131; 607/60
    See application file for complete search history.

(56) References Cited

U.S. PATENT DOCUMENTS

| 3,182,129 | A |   | 5/1965 | Clark et al. ............... 179/1 |
|---|---|---|---|---|
| 3,233,041 | A |   | 2/1966 | Croslin ................... 179/1 |
| 3,387,149 | A |   | 6/1968 | Young .................. 310/8.5 |
| 3,555,187 | A |   | 1/1971 | Rowley ................... 179/1 |
| 3,573,394 | A |   | 4/1971 | Birnbaum ............... 128/2.05 |
| 3,846,585 | A |   | 11/1974 | Slosberg et al. ........... 179/1 |
| 3,882,277 | A | * | 5/1975 | DePedro et al. ....... 379/106.02 |
| 4,337,377 | A | * | 6/1982 | Van Riper et al. ..... 379/106.02 |
| 4,458,687 | A | * | 7/1984 | Dickson ................ 600/397 |
| 4,723,555 | A |   | 2/1988 | Shue .................... 128/715 |
| 4,883,064 | A | * | 11/1989 | Olson et al. ............ 600/509 |
| 5,027,825 | A | * | 7/1991 | Phelps et al. ........... 600/528 |
| 5,550,902 | A | * | 8/1996 | Abbruscato ........... 379/106.02 |
| 5,704,364 | A |   | 1/1998 | Saltzstein et al. ......... 128/696 |
| 5,717,769 | A |   | 2/1998 | Williams ................ 381/67 |
| 5,774,563 | A |   | 6/1998 | DesLauriers et al. ........ 381/67 |
| 5,841,846 | A |   | 11/1998 | Abbruscato ........... 379/106.02 |
| 5,952,618 | A |   | 9/1999 | Deslauriers .............. 181/131 |
| 6,002,777 | A |   | 12/1999 | Grasfield et al. ........... 381/67 |
| 6,014,432 | A |   | 1/2000 | Modney .............. 379/106.02 |
| 6,134,331 | A |   | 10/2000 | Baekgaard ............... 381/67 |
| 6,324,289 | B1 |   | 11/2001 | Orten .................... 381/67 |
| 6,378,648 | B1 |   | 4/2002 | Werblud ................. 181/131 |
| 6,485,416 | B1 | * | 11/2002 | Platt et al. ............... 600/300 |

(Continued)

FOREIGN PATENT DOCUMENTS

WO    WO 98/34542    8/1998

(Continued)

OTHER PUBLICATIONS

Brown, S. G., *A Telephone Relay* paper, 1910.

(Continued)

*Primary Examiner*—Robert E. Pezzuto
*Assistant Examiner*—Eric Bertram
(74) *Attorney, Agent, or Firm*—Wilmer Cutler Pickering Hale and Dorr LLP

(57) ABSTRACT

The invention provides a stethoscope device comprising a chest piece, an amplifier and a mixer compatible with a conventional voice quality telephone system. Electrical signals are generated that are representative of physiological sounds such as breath sounds, heart sounds and bowel sounds. The electrical signals can be combined with voice communications at the remote site and transmitted over the telephone system. The invention also provides a system and method for diagnosis by a trained health care professional with the patient being located at a remote site. In another embodiment, the invention also provides a system and method for training students to interpret stethoscope sounds. In addition, the system allows for simultaneous listening by the health care professional and another individual at the remote location of the stethoscope.

20 Claims, 6 Drawing Sheets

U.S. PATENT DOCUMENTS 6,726,635 B1 * 4/2004 LaSala ................. 600/528

FOREIGN PATENT DOCUMENTS

| WO | WO 00/49549 | 8/2000 |
| WO | WO 01/33457 | 5/2001 |
| WO | WO 02/24074 | 3/2002 |

OTHER PUBLICATIONS

Frederick, H. A., et al., *"The Stethophone," An Electrical Stethoscope*, 1924 The Bell System Technical Journal, pp. 531-549.

Murphy, R. L. H., et al., *Accuracy of Cardiac Auscultation by Microwave*, 1973 Chest, vol. 63, No. 4, pp. 578-581.

Mattioli L., et al., *Pediatric Cardiology: Auscultation from 280 Miles Away*, 1992 Kansas Medicine, pp. 326-350.

Belmont, J. M., et al., *Evaluation of Remote Stethoscopy for Pediatric Telecardiology*, 1995 Telemedicine Journal, vol. 1, No. 2, pp. 133-149.

Pasterkamp, H., *Respiratory Sounds Advances Beyond the Stethoscope*, 1997 Am J Respir Crit Care Med, vol. 156, pp. 974-987.

* cited by examiner

STETHOSCOPIC SYSTEMS AND METHODS

BACKGROUND OF THE INVENTION

Normal and various pathological conditions of a patient can be revealed by auscultation examination, listening for physiological sounds from the interior of the body, to determine the condition of the lungs, heart, arteries, veins, intestines, pleura and other organs. This examination is generally performed with an instrument called a stethoscope. A stethoscope examination is a fundamental medical examination procedure that is part of any routine examination performed by a physician. A stethoscope examination allows the physician to analyze a patient's cardiovascular and respiratory system. To perform this analysis, the doctor uses an acoustic stethoscope to listen to the sounds generated by the patient's cardiovascular and respiratory system. The typical examination involves a doctor placing a stethoscope bell-and-diaphragm chest piece on a patient's back or chest so that the doctor is able to listen to sounds at various locations on the patient's body. The bell acts as a filter to isolate sounds in a lower frequency range, while the diaphragm filters out lower frequencies and passes higher frequency stethoscope sound.

Although a stethoscope examination is a simple and routine procedure, it nevertheless requires that a patient be present with the doctor in an examination room. Consequently, those patients who may require frequent, perhaps even daily, stethoscope examinations are burdened by the administrative, financial, and logistical hardships involved in frequent visits to a doctor.

Patients who live a long distance from a doctor's office are particularly burdened. Patients residing in a remote location with a need to frequently see a doctor must either be admitted into a hospital (or other local facility), or be willing to hire a health care professional to visit or stay with the patient at the patient's home. For most patients, today's spiraling medical costs place both of these options out of reach. There exists a compelling need, therefore, for a system by which a doctor can perform medical examinations on a remotely-located patient while avoiding at least some of the usual administrative, financial, and logistical hardships.

Traditional stethoscopes have amplified and filtered sounds by acoustic means. Acoustic stethoscopes include a "chest piece" that is brought into contact with the patient's skin, and two flexible tubes, terminating in earpieces placed in the health care professional's ears. More recently, stethoscopes have been developed that use electronic amplification and filtering.

The use of various sensors that transform internal body sounds into electrical voltages is well known in the art. Various types of transducers have been used in implementing body sound sensors, including both air coupled and contact microphones and accelerometers. Combined acoustic and electronic stethoscopes are also known in the art.

Conventional acoustic stethoscopes generally operate in the range of about 10 Hz to about 1 kHz, while electronic stethoscopes generally have higher sensitivity and an extended high frequency range.

Modem systems for transmitting stethoscopic output over a telephone system have involved elaborate analog and digital processing steps in various attempts to compensate for the frequency characteristics of the telephone system. Exemplary analog processing steps include using the output of a stethoscope to modulate a carrier frequency that is within the bandwidth of a plain old telephone service (POTS) and shifting the frequency of the stethoscopic signal into the bandwidth of a POTS. Digital stethoscopic systems transmit a digital representation of the stethoscopic signal over the POTS or use the POTS to access a network, such as the Internet. All of the above systems have required additional equipment beyond the stethoscope and telephone at the remote site and specialized equipment at the diagnostic site.

There remains a need for a cost-effective stethoscopic system usable at different locations, for example, at a site remote from a health care professional.

SUMMARY OF THE INVENTION

The system and method of the present invention includes a stethoscopic device that produces an electrical signal representative of physiological sounds, an amplifier that amplifies the signal produced by the stethoscopic device, a mixer that combines the amplified signal and the output of a communication compatible ear piece such as, a telephone ear piece and mouthpiece and an operative link to the telephone system, such that a health care professional can access the signal representative of physiological sounds using conventional voice quality access to the telephone system.

In one preferred embodiment, a remote stethoscope system comprises a stethoscopic device that includes an acoustic device operatively linked to a microphone by an acoustic conduit and that produces electrical signals representative of physiological sounds; an amplifier that amplifies the electrical signals produced by the microphone; a signal mixer that combines the amplifier output and the output of a telephone handset; and an operative link to the telephone system, wherein the remote stethoscope system can be accessed by a health care professional using only a telephone. In a preferred embodiment, the stethoscopic device includes an acoustic transducer, more preferably an acoustic transducer tuned to amplify physiological sounds of a subject body, such as, for example, a mammalian body, most preferably an acoustic transducer tuned to amplify physiological sounds of a human body. Alternatively, the stethoscopic device can include a piezoelectric or electromagnetic transducer that converts physiological sounds into electrical signals.

The amplifier is chosen to provide an input impedance, frequency response and sensitivity appropriate to amplify the electrical signals produced by the stethoscopic device to a level that is comparable to signals produced and received by a conventional telephone ear piece and mouthpiece. The amplification can be adjusted by the user using conventional means, such as a variable resistor. In preferred embodiments, the amplifier output can be monitored at a site, for example, remote using a speaker or headphone. In one embodiment, the amplifier has a sufficiently high output impedance that the amplifier draws less than 10% of the current that a conventional handset draws from the telephone system.

The mixer serves to combine the electrical signal produced by the amplifier with the electrical signal transmitted and received by the ear piece and mouthpiece of a conventional telephone handset. In embodiments in which the output signal and output impedance of the amplifier are compatible with the electrical signal sent and received by the ear piece and mouthpiece of a conventional telephone handset, the mixer can be a simple passive "Y" connector. Alternatively, the mixer may serve to match impedances, and may be designed to amplify or attenuate the signal representative of the physiological sounds with respect to electrical signals sent and received by the ear piece and mouthpiece of a conventional telephone handset.

The output of the mixer is in communication with the input of an operative link to the telephone system. In some preferred embodiments, the operative link is the base unit of a telephone that has a hard-wired connection to the telephone system through a landline. In other embodiments, the operative connection to the telephone system is through a wireless link.

A health care professional has access to the remote stethoscopic system using a conventional means of access to the voice quality telephone system. The access can be by using a telephone unit connected to the telephone system by wireless or wired connections. The accessed physiological sounds can be recorded and further analyzed off-line.

In one embodiment, the system of the present invention provides a method of listening to sounds indicative of a physiological condition produced by a subject, such as, for example, a mammal at a site remote from the health care professional. These sounds can include heart sounds, arterial sounds, lung sounds, and bowel sounds. The method comprises the steps of placing a stethoscopic device having a chest piece in contact with the body surface of a subject that is producing physiological sounds at a first site, converting the sounds indicative of a physiological condition into electrical signals representative of the sounds, amplifying the electrical signals, combining the amplified electrical signals with electrical signals received and transmitted by a telephone handset, transmitting the combined signal via an operative link to the telephone system, accessing the telephone system at a second site using telephone equipment, and at the second site listening to the sounds indicative of a physiological condition produced by a subject at the first site.

In another embodiment, a method of the present invention provides for a health care professional to diagnose the condition of a patient at a remote site, comprising the steps of accessing the telephone system from a site remote from the patient using conventional voice telephone equipment, directing the placement of a stethoscopic device having a chest piece in contact with the body surface of a patient producing physiological sounds, listening to the physiological sounds, wherein the physiological sounds have been converted into electrical signals representative of the physiological sounds, the electrical signals amplified, the amplified electrical signals combined with electrical signals received and transmitted by a telephone handset, and the combined signal transmitted via an operative link to the telephone system, and diagnosing the condition of the patient using the information conveyed by the physiological sounds.

In another embodiment, the invention provides a system and method for teaching or consultation whereby multiple auditors at a first and a second site can listen to sounds indicative of a physiological condition that are produced by a patient at one site. The system is interactive in that a health care professional at a site remote from the patient can direct the placement of the remote stethoscope on the surface of the patient to optimize detection's of sounds characteristically indicative of physiological conditions. The remote stethoscope can be placed at the health care professional's direction by the patient, or preferably, by an agent at the remote site. Such a system is particularly useful for training students to recognize stethoscope sounds or for consultation by an expert at a distant site.

The foregoing and other features and advantages of the stethoscopic system and methods will be apparent from the following more particular description of preferred embodiments of the system and method as illustrated in the accompanying drawings in which like reference characters refer to the same parts throughout the different views.

BRIEF DESCRIPTION OF THE DRAWINGS

The drawings are not necessarily to scale, emphasis instead being placed upon illustrating the principles of the invention.

DETAILED DESCRIPTION OF THE INVENTION

The present invention provides a stethoscopic system and a method of using the stethoscopic system at different locations, such as a patient located at a site that is remote from a health care professional. The system provides access for a health care professional to the audible sounds of a patient which are indicative of a physiological condition.

In order to be generally available at the largest number of remote locations, a stethoscopic system is functional using the voice telephone system, also known as the "plain old telephone service" (POTS). The voice bandwidth of the telephone system has a practical range (greater than or equal to 90% of maximum response) of 300 Hz–3 kHz with a peak at about 1 kHz.

Physiological sounds are complex, including a fundamental frequency and overtones. Table 1, below, summarizes basic frequency information about heart sounds.

TABLE 1

BASIC HEART SOUNDS

| Sounds | Fundamental Frequency | Overtones |
|---|---|---|
| Systolic | 40–80 Hz | Up to 4 kHz |
| Diastolic | 60–100 Hz | Up to 4 kHz |
| Systolic & Diastolic Murmurs | 300–800 Hz | |

Table 2, below, summarizes basic frequency information regarding respiratory sounds.

TABLE 2

MAJOR CATEGORIES OF RESPIRATORY SOUNDS

| Respiratory Sound | Mechanisms | Origin | Acoustics | Relevance |
|---|---|---|---|---|
| Basic sounds | | | | |
| Normal lung sound | Turbulent flow vortices, unknown mechanisms | Central airways (expiration), lobar to segmental airway (inspiration) | Low-pass filtered noise (range <100 Hz to >1,000 Hz) | Regional ventilation, airway caliber |
| Normal tracheal sound | Turbulent flow, flow impinging on airway walls | Pharynx, larynx, trachea, large airways | Noise with resonances (range <100 to >3,000 Hz) | Upper airway configuration |
| Adventitious sounds | | | | |
| Wheeze | Airway wall flutter, vortex shedding | Central and lower airways | Sinusoid (range ~100 to >1,000 HZ; duration, typically >80 ms) | Airway obstruction, Flow limitation |
| Rhonchus | Rupture of fluid films, airway wall vibrations | Larger airways | Series of rapidly dampened sinusoids (typically <300 Hz and duration >100 ms) | Secretions, abnormal airway collapsibility |
| Crackle | Airway wall stress-relaxation | Central and lower airways | Rapidly dampened wave deflection (duration typically <20 ms) | Airway closure, secretions |

This table lists only the major categories of respiratory sounds and does not include other sound such as, for example, squawks, friction rubs, grunting, snoring, or cough. Current concepts on sound mechanisms and origin are listed but these concepts may be incomplete and unconfirmed.

Figure 1:
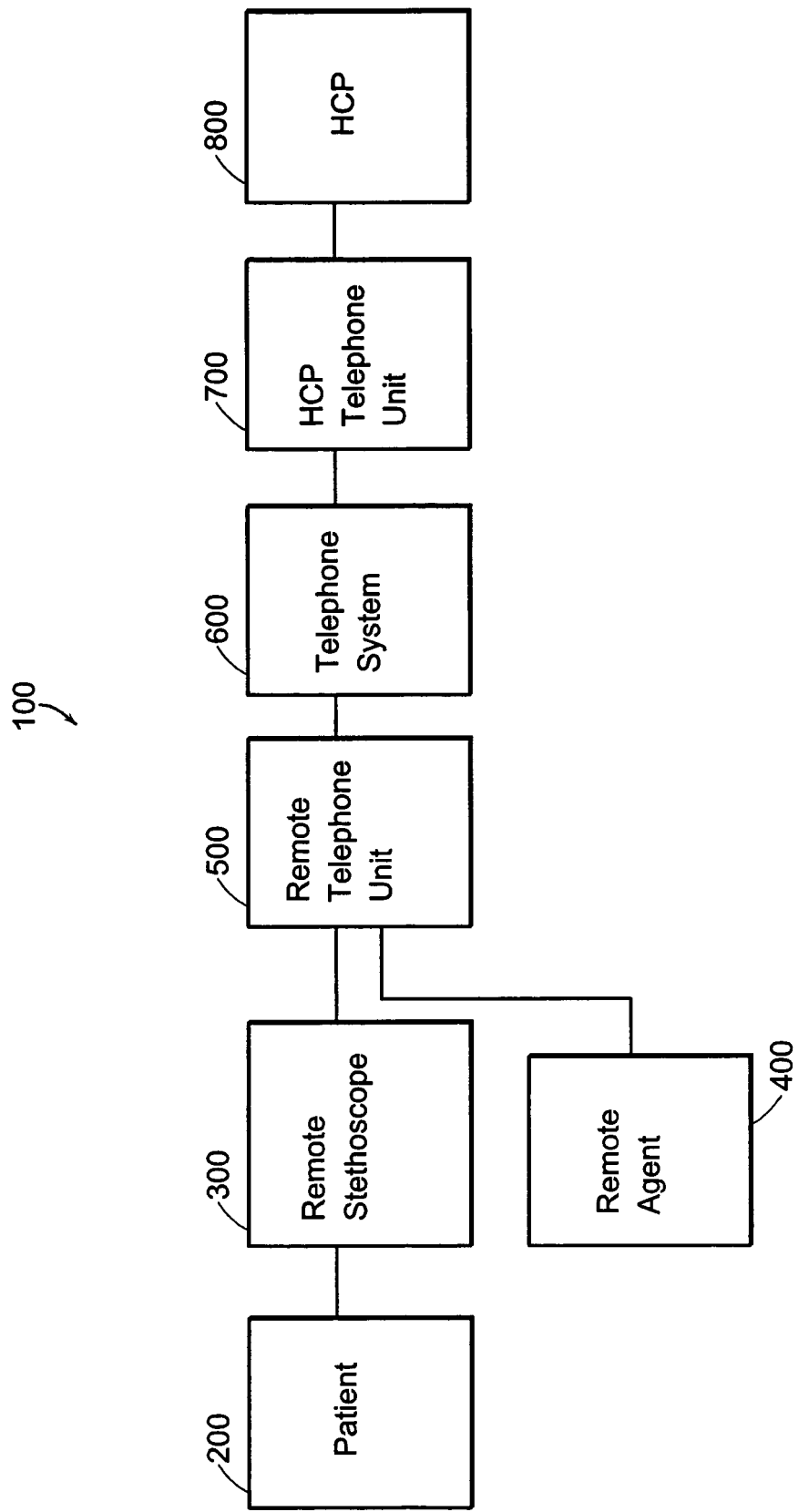
FIG. 1 is a block drawing illustrating the components of a preferred embodiment of a stethoscope system in accordance with the present invention.

FIG. 1 is a block drawing illustrating the relationship of components of an embodiment of a stethoscopic system 100. A patient 200 can be situated, for example, at a location that is physically remote from the location of a health care professional (HCP) 800. The location of the patient 200 and the health care professional 800 are in communication through a telephone system 600, a telephone unit 500 and HCP telephone unit 700, respectively. In some preferred embodiments, an agent 400 is present to operate the stethoscope 300, observe the patient 200 and verbally interact with the health care professional 800. Such embodiments are especially suitable if the patient 200 is a child, cannot communicate effectively with the health care professional 800 or cannot operate the stethoscope 300 without assistance. In other embodiments, in which the patient 200 is capable of operating the stethoscope 300 and communicating with the health care professional 800, the patient 200 can carry out the functions otherwise performed by the agent 400.

Figure 2:
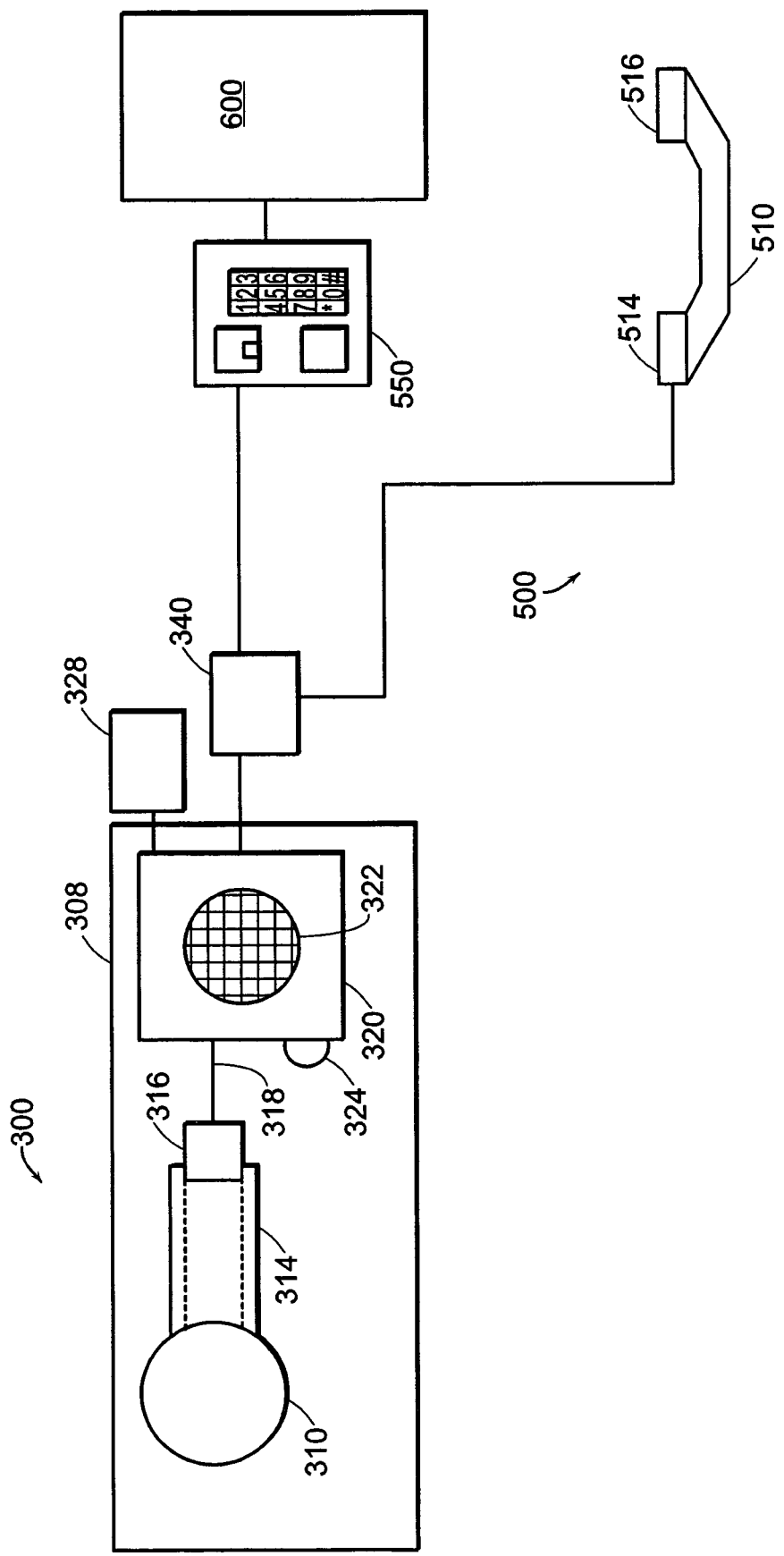
FIG. 2 is a schematic drawing of a preferred embodiment of the remote stethoscope system, showing the relationships between stethoscope, a remote telephone unit and telephone system in accordance with the present invention.

FIG. 2 is a schematic drawing of an embodiment of the remote stethoscope system, showing the relationships between remote stethoscope 300, remote telephone unit 500 (comprising handset 510 and base unit 550) and telephone system 600. In one embodiment, the remote stethoscope 300 comprises a vibration transducer 310 acoustically linked to a microphone 316, an amplifier 320 that amplifies the electrical signal produced by the microphone 316 and a mixer 340 that combines the amplified electrical signal from the amplifier 320 with the electrical signal produced by the handset 510 of the remote telephone unit 500.

A stethoscope acoustic vibration transducer, or "chest piece" 310 transfers the acoustic signal from the living organism such as, for example, a human, an animal, to the rest of the apparatus. In preferred embodiments, the chest piece may be designed to attenuate or amplify desired sound frequency bands using resonance. The acoustic signal is transmitted along an acoustic conduit 314 such as, for example, a simple flexible plastic tube to a microphone 316 that is operatively coupled to the acoustic conduit 314. The microphone converts the acoustic signal to an electrical signal. Suitable microphones include, for example, omnidirectional microphones such as an electret microphone which is sensitive, durable, compact in size and has low power requirements. Most lavalier (tie-clip) microphones, consumer video camera microphones, and microphones used with computer sound cards, which is applicable in a preferred embodiment of the present invention, are electret microphones. The electret microphone is a modification of the capacitor or condenser microphone, which exploits changes in capacitance due to mechanical vibrations to produce voltage variations proportional to sound waves. Whereas condenser microphones need an applied voltage, the electret has a built-in-charge, and the few volts needed are to power a built in field emitter transistor (FET) buffer, not to create an electric field. An electret microphone capsule can be a two-terminal device or alternatively a three-pin capsule. The two-pin device approximates a current source when biased with 1–9 volts and consumes less than half a milliamp. An alternative embodiment includes a battery powered electret microphone having a circuit that can be used with tape recorders and sound cards designed for dynamic microphones. In another embodiment, power can be supplied to the microphone via a microphone signal cable.

The microphone suitably has a sensitivity matched to the sound source, for example, −65 db (+/−3 db) at 1 kHz, where 0 db=1V/microbar. In one embodiment, the microphone has an impedance of 1 k-ohm at 1 kHz. The frequency response of the microphone is preferably broader than the 300–3400 Hz bandwidth of the telephone system. In one preferred embodiment the frequency response of the microphone is in the range of about 70 Hz to about 16 kHz.

The electrical signal output of the microphone is conducted by a wire 318 to the input of an amplifier 320. The relative lengths of the acoustic conduit 314 and the wire 318 are suitably chosen to provide ease of use and minimize the effects of ambient noise. It is known that choice of the length of an acoustic conduit is one factor that can determine the resonant frequency of the system, and can serve to enhance the intensity of low frequency physiological sounds before these sounds are converted into electrical signals (in its entirety). In a preferred embodiment the amplifier is battery operated, has an input sensitivity of 1 mV, an input impedance of 5 k-ohms, a power output of 200 mW at 1 kHz into a 16 ohm load, with <2% total harmonic distortion at an output of 200 mW at 1 kHz and a frequency response of about 100 Hz to about 10 kHz.

In preferred embodiments the amplifier 320 is configured in a housing that optionally contains a speaker 322 and a control 324 that regulates volume of the speaker 322. Control 324 optionally includes the gain control and is the ON/OFF switch for the amplifier 320. In preferred embodiments the amplifier 320 is battery powered, and has an AC adapter 328 that serves to recharge the batteries. The speaker 322 can be used to monitor the acoustical signal at the remote location, thereby facilitating interaction between the remote agent and the patient with the health care professional. In addition, the speaker allows several people at the patient's location to hear the same sound, thereby providing a system that is suitable for training purposes. In a preferred embodiment the components of the system is enclosed in a housing 308.

The output of the amplifier 320 is connected to a mixer 340 that combines the electrical signal produced by the remote stethoscope 300 with the electrical signal produced by the handset 510 of the remote telephone unit 500. The remote telephone unit can be connected to the telephone system 600 by a landline or, alternatively, be connected by a wireless connection.

Figure 3:
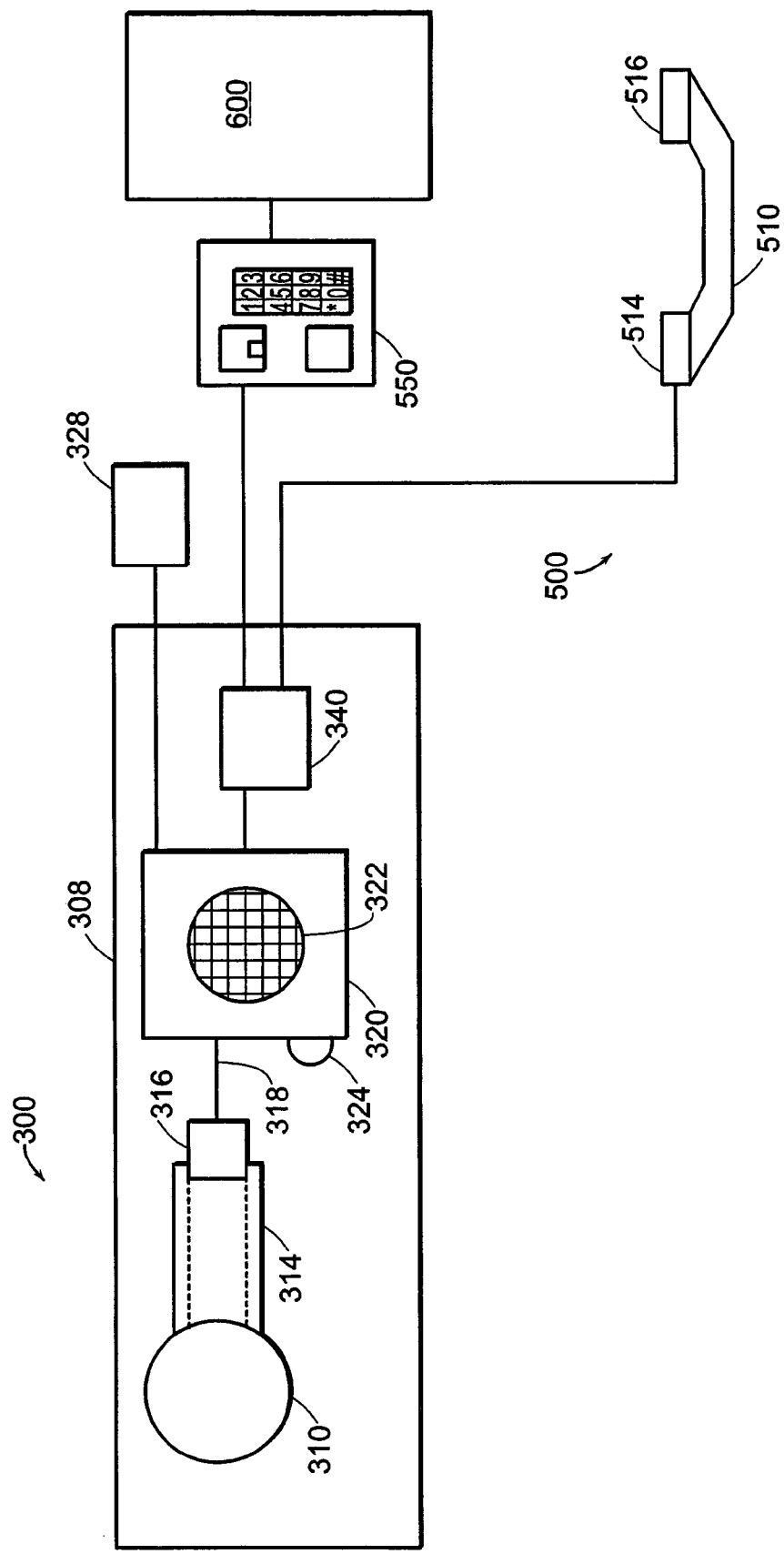
FIG. 3 is a schematic diagram of another preferred embodiment of the remote stethoscope system.

The mixer 340 may be separate as illustrated in FIG. 2 or contained within the same housing 308 as illustrated in FIG. 3 as the amplifier 320 and speaker 322. In some embodiments the mixer 340 can be a simple 'Y' connector. In one embodiment the output impedance of the amplifier 320 is selected to minimize cross talk between the remote stethoscope 300 and the handset 510, to the extent that conversational sounds received at the microphone 514 of the handset do not mask the physiological sounds heard at the speaker 322. In several embodiments the handset 510 is connected by the handset cord to the mixer 340. The output of the mixer 340 is connected to the remote telephone base unit 550 which, in turn, is operatively connected to the telephone system 600. In preferred embodiments the output of the mixer 340 is connected to the connector normally occupied by the handset cord. In embodiments in which the remote telephone unit 500 is a cordless telephone, the mixer 340 combines the electrical signal produced by the remote stethoscope 300 with the electrical signal produced by an external headset 510 that is compatible with the remote telephone unit and the output of the mixer is connected to the external headset jack of the cordless telephone handset. In embodiments in which the remote telephone unit 500 is a wireless telephone, the mixer 340 combines the electrical signal produced by the remote stethoscope 300 with the electrical signal produced by an external headset 510 that is compatible with the remote telephone unit and the output of the mixer is connected to the external headset jack of the wireless telephone.

In a preferred embodiment, the stethoscope was constructed as described above, using an acoustic transducer and acoustic conduit, electret microphone, such as, for example, provided by Radio Shack No. 330-3013 and an integrated amplifier and speaker, such as, for example, provided by Radio Shack No. 277-1008SC. The amplifier output is connected using a "Y" connector to the handset and base unit of a conventional telephone.

In measurements taken with volunteer subjects, sounds indicative of a physiological condition were recognized by listeners at a location remote from the patient over the conventional voice quality telephone system. The device provides breath sounds, which are identifiable by listeners. Each listener identified the sounds of wheezing correctly. Summarizing the measurements with respect to breath sounds for three adult patients, who were examined with a preferred embodiment of the stethoscopic system over lung fields with five separate listeners, the listeners identified breath sounds correctly for each subject. For the same subjects, the same five listeners were able to identify the sounds associated with wheezing correctly in each subject. During deep breathing, when the stethoscope was held over the trachea/neck region, the sounds were described as different in character than when the device was placed over the lung fields. With respect to heart sounds for the three adult patients, when examined with the device of a preferred embodiment located over the cardiac region, two of the three listeners were able to identify heart sounds and count the pulse accurately.

For adolescent patients, with respect to breath sounds, when examined with the present invention stethoscope over lung fields, three separate listeners identified breath sounds correctly for each subject. For the same subjects, the same three listeners were able to identify wheezing correctly in each subject. During deep breathing, when the stethoscope was held over the trachea/neck region, the sounds were described as different in character than when the device was placed over the lung fields. With respect to the heart sounds of the two adolescent patients, when examined with the device located over the cardiac region, three separate listeners were able to identify heart sounds and count the pulse rate accurately.

For two toddlers examined with a preferred embodiment of the stethoscopic system over lung fields with respect to breath sounds, two separate listeners identified breath sounds correctly for each subject. The wheezing exam was not performed on the toddler subjects. Neck region auscultation was also not performed on the toddlers. As for heart sounds, the two toddlers when examined with the device located over the cardiac region, two separate listeners were able to identify heart sounds and count the pulse rate accurately.

Figure 4:
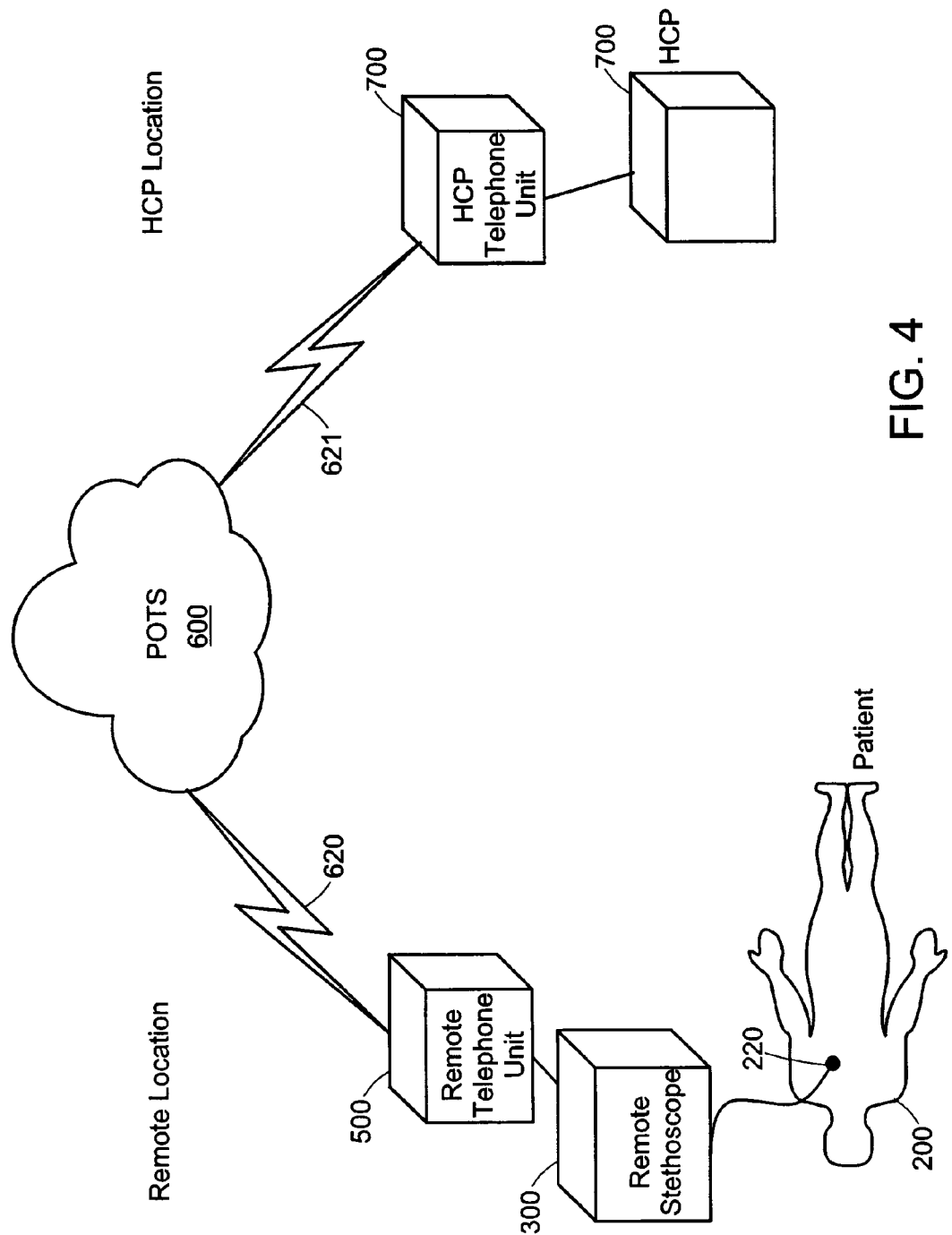
FIG. 4 is a schematic diagram of one preferred embodiment of the remote stethoscope system in use.

FIG. 4 is a schematic diagram showing one embodiment of the stethoscopic system in use. The stethoscope 300 collects sounds from a site 220 on the patient 220 and produces an electrical signal representative of the sounds that is conveyed by an operative connection to a remote telephone unit 500. The remote telephone unit 500 conveys the electrical signal to the telephone system 600 by an operative link 620. Link 620 can be a land link, or a RF link. Similarly, link 621 between the telephone system 600 and the HCP telephone unit 700 can be a land line or a wireless link, for example, a radio frequency (RF) link. The health care practitioner listens to the sounds produced by the HCP.

Figure 5:
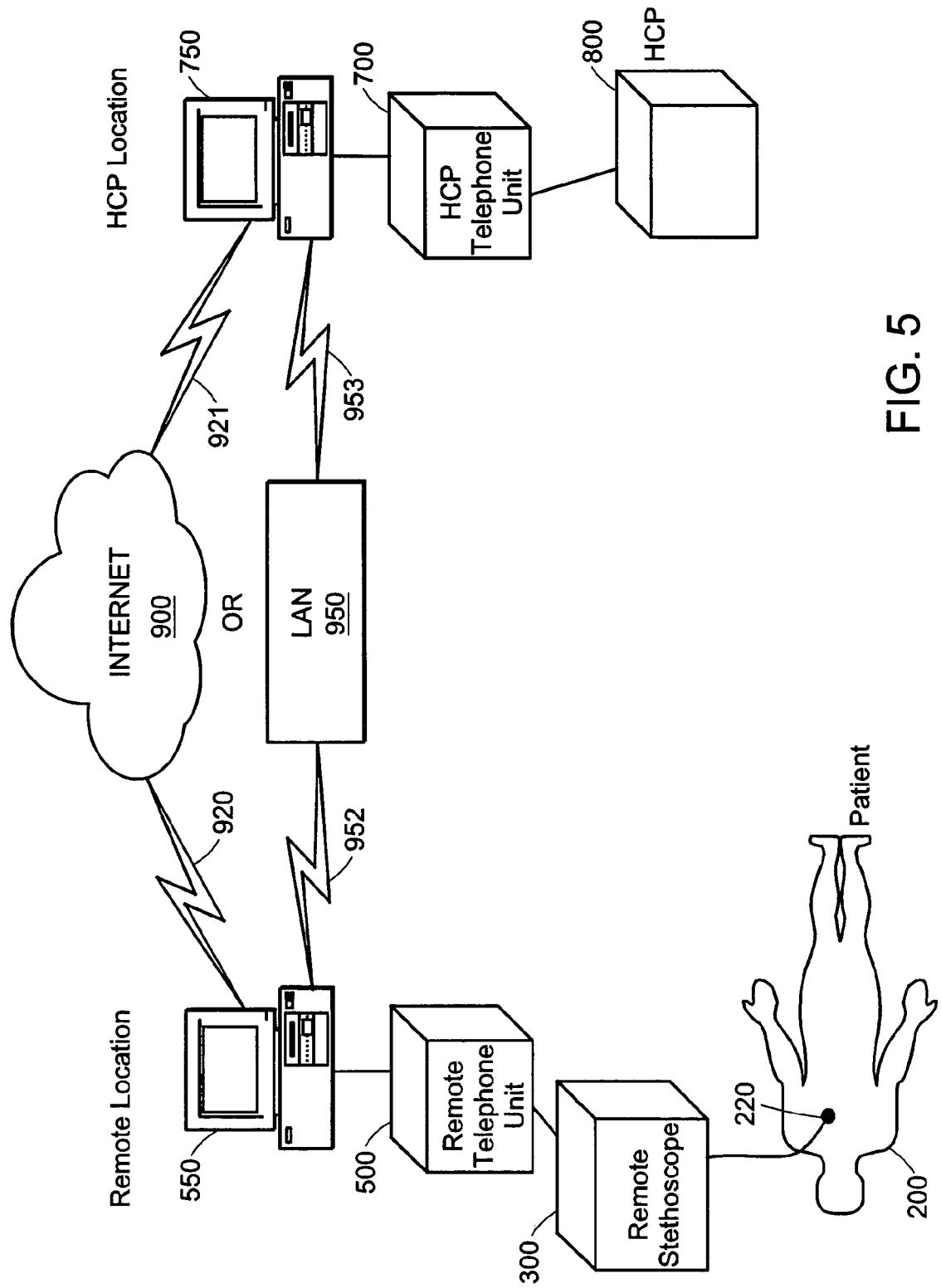
FIG. 5 is a schematic diagram of another preferred embodiment of the remote stethoscope system in use.

FIG. 5 is a schematic diagram showing an embodiment in which computers 550 and 750 are used to transmit digital signals to and from a packet switch network, for example, the Internet 900 or a local area network (LAN) 950 corresponding to the electrical signals produced by the remote telephone unit 500 and the HCP telephone unit 700. As in FIG. 4, the remote stethoscope 300 collects sounds from a site 220 on the patient 200 and produces an electrical signal representative of the sounds that is conveyed by an operative connection to a remote telephone unit 500.

The remote telephone unit 550 is operatively linked to a remote location computer 550. The remote location computer can be, for example, and without limitation, a notebook computer, a desktop computer, a personal digital assistant, or a hand held personal computer (PC), or a pocket PC.

In a preferred embodiment, the computer located at the remote location runs an operating system with a graphical user interface. In a preferred embodiment, the computer 550 is configured to exchange numeric data, text and images with the HCP location computer 750.

In a preferred embodiment one or more of links 920, 921, 952 and 953 is a RF link. Alternatively, links 920, 921, 952 and 953 can be implemented in part using land lines. As in the embodiment depicted in FIG. 4, the health care practitioner listens to the sounds produced by the HCP. In a preferred embodiment, a device, such as, for example, a tape recorder, to store the auditory signals may be added to the system for post collection analysis. An alternate embodiment uses voice over Internet protocol to transmit voice conversations over a data network using the Internet protocol. Such a data network can be, for example, the Internet or a wide area network. Thus the voice, or more specifically, the audible signals indicative of the physiological condition can be communicated over packet networks.

Figure 6:
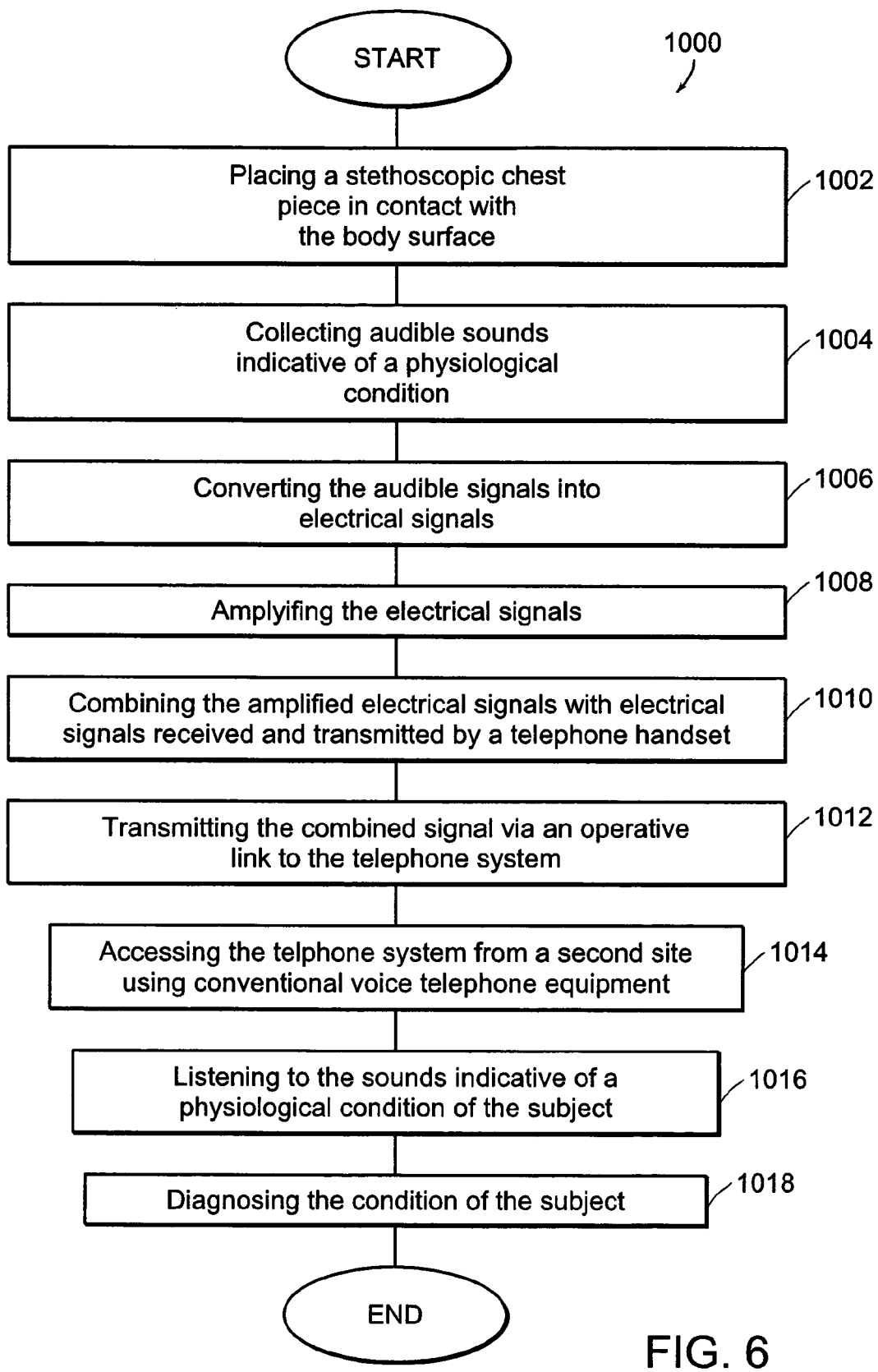
FIG. 6 is a flowchart illustrating a method in accordance with a preferred embodiment of the present invention.

FIG. 6 illustrates a flowchart in accordance with a method of a preferred embodiment of the present invention. Per step 1002 a chest piece of a stethoscopic device is placed in contact with a body surface, preferably the chest of a subject requiring an examination. The audible sounds indicative of a physiological condition are collected as per step 1004. Per step 1006, the method further comprises converting the audible signals into electrical signals. The electrical signals are then amplified in step 1008. The method includes combining the amplified electrical signals with the electrical signals received and transmitted by a telephone handset in step 1010. Per step 1012 the combined signal is transmitted via an operative link to the telephone system. The HCP accesses the telephone system at a second site using conventional telephone equipment per step 1014. The HCP listens to the sounds indicative of a physiological condition of the subject per step 1016 and can diagnose the condition of the subject per 1018.

It should be understood that the programs, processes, methods and systems described herein are not related or limited to any particular type of collection media, or computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, other embodiments in hardware or firmware implementations may alternatively be used, and vice-versa.

It will be apparent to those of ordinary skill in the art that methods involved in the stethoscopic system and method may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

The claims should not be read as limited to the described order or elements unless stated to that effect. Therefore, all embodiments that come within the scope and spirit of the following claims and equivalents thereto are claimed as the invention.

What is claimed:

1. A stethoscopic system comprising:
 a stethoscopic device having a chest piece that collects a first signal representative of physiological sounds from a subject;
 an amplifier that amplifies the signal collected by the stethoscopic chest piece to result in an amplified signal, wherein the amplified signal has the same frequency spectrum as the first signal;
 a mixer that combines the amplified signal and an output of a telephone compatible ear piece and mouthpiece, wherein the mixer output signal has the same frequency spectrum as the first signal; and
 an operative link to a telephone system, wherein the mixer output signal indicative of physiological sounds is accessed over the telephone system.

2. The stethoscopic system of claim 1 wherein the chest piece comprises an acoustic transducer operatively coupled to a microphone by an acoustic conduit.

3. The stethoscopic system of claim 2 wherein the microphone comprises an electret microphone.

4. The stethoscopic system of claim 1 wherein the chest piece comprises a piezoelectric transducer.

5. The stethoscopic system of claim 1 wherein the chest piece comprises an electromagnetic transducer.

6. The stethoscopic system of claim 1 further comprising a telephone at a site remote from the subject being accessed.

7. The stethoscopic system of claim 1 wherein the operative link further comprises at least one wireless link.

8. The stethoscopic system of claim 7 wherein the at least one wireless link comprises a radio frequency link.

9. The stethoscopic system of claim 1 wherein the operative link comprises a wired connection to the telephone system.

10. The stethoscopic system of claim 1 wherein the signals indicative of physiological sounds comprises signals associated with respiration and cardiac activity collected from lungs, trachea and heart regions of the subject.

11. A method of listening to acoustic signals indicative of a physiological condition produced by a subject at a first site comprising the steps of:
 placing a stethoscopic chest piece in contact with the body surface of the subject producing sounds indicative of the physiological condition at the first site;
 converting the sounds into a first electrical signal representative of the physiological sounds;
 amplifying the first electrical signal, wherein the amplified signal has the same frequency spectrum as the first electrical signal;
 combining the amplified electrical signal with electrical signals received and transmitted by a telephone handset, wherein the combined signal has the same frequency spectrum as the first electrical signal;

transmitting the combined signal via an operative link to a telephone system;

accessing the telephone system at a second site using conventional voice telephone equipment; and listening to the sounds indicative of the physiological condition produced by the subject at the first site to diagnose a physiological condition.

12. The method of claim 11 wherein the acoustic signals comprise signals associated with respiration and cardiac activity collected from the lungs, trachea and heart regions of the subject.

13. The method of claim 11 wherein the operative link comprises a wired connection to the telephone system.

14. The method of claim 11 wherein the operative link further comprises at least one wireless link.

15. The method of claim 14 wherein the at least one wireless link comprises a radio frequency link.

16. A method for diagnosing the condition of a patient at a remote site, comprising the steps of:

accessing a telephone system at a first site remote from the patient at a second site using voice telephone equipment;

directing the placement of a stethoscopic device having a chest piece in contact with the body surface of the patient producing sounds indicative of a physiological condition;

listening to the physiological sounds at the first site, wherein the physiological sounds have been converted into a first electrical signal representative of the physiological condition, the first electrical signal being amplified, the amplified electrical signal combined with the electrical signals received and transmitted by a telephone handset, wherein the amplified and combined signal have the same frequency spectrum as the first signal, and the combined signal transmitted via an operative link to the telephone system; and diagnosing the condition of the patient using the information conveyed by the physiological sounds.

17. The method of claim 16 wherein the electrical signals comprise signals collected from the lungs, trachea and cardiac regions of the patient and are indicative of respiratory and cardiac activity.

18. The method of claim 16 wherein the operative link comprises at least one wireless link.

19. The method of claim 16 wherein the operative link comprises a wired connection to the telephone system.

20. A method for diagnosing a respiratory condition by a plurality of professionals at a first and a second site as they listen to the sounds indicative of a physiological condition produced by a patient, comprising the steps of:

accessing a telephone system at a first site remote from the patient using conventional voice telephone equipment;

directing the placement of a stethoscopic device having a chest piece in contact with the body surface of a patient producing sounds indicative of a physiological condition;

wherein at least one professional present at the first site and at least one professional present at the second site can listen to the sounds indicative of the physiological condition and wherein the sounds are converted into first electrical signals representative of the physiological sounds, the electrical signals being amplified, the amplified electrical signals combined with the electrical signals received and transmitted by a telephone handset, wherein the amplified electrical signals and the combined electrical signals have the same frequency spectrum as the first electrical signals; and the combined signal transmitted via an operative link to the telephone system.

* * * * *